United States Patent [19]

Bergmans

[11] Patent Number: 4,729,238
[45] Date of Patent: Mar. 8, 1988

[54] DEVICE FOR MEASURING THE VOLUME OF A GAS

[75] Inventor: Anthony B. Bergmans, Bilthoven, Netherlands

[73] Assignee: Gould Electronics, B.V., Bilthoven, Netherlands

[21] Appl. No.: 864,794

[22] Filed: May 19, 1986

[30] Foreign Application Priority Data

May 21, 1985 [NL] Netherlands ................... 8501449

[51] Int. Cl.⁴ ........................... G01F 3/14; F15B 21/00
[52] U.S. Cl. ........................................ 73/239; 92/83; 92/98 D
[58] Field of Search ............... 73/3, 239, 240, 242, 73/269, 272, 278; 92/80, 83, 86.5, 98 D, 102

[56] References Cited

U.S. PATENT DOCUMENTS 2,678,663  5/1954  Thyba ................................. 92/102
2,725,078  11/1955 Glancy ............................... 92/98 D
3,722,506  3/1973  McMillan, Jr. ................ 92/98 D X
3,769,879  11/1973 Lofquist, Jr. .................... 92/98 D X
4,096,855  6/1978  Fleury, Jr. ......................... 73/239 X Primary Examiner—Herbert Goldstein
Attorney, Agent, or Firm—M. Lawrence Oliverio; Therese A. Hendricks

[57] ABSTRACT

A device for measuring the volume of a gas comprises a cylinder and a piston movably mounted in the cylinder. A first membrane sealingly connects the piston with the inner wall of the cylinder. The cylinder, the piston and the first membrane determine a measuring space in which a measuring conduit for the gas to be measured debouches. A second membrane also sealingly connects the piston with the cylinder inner wall. The first and second membranes determine an intermediate space in which an underpressure is generated during operation.

7 Claims, 3 Drawing Figures

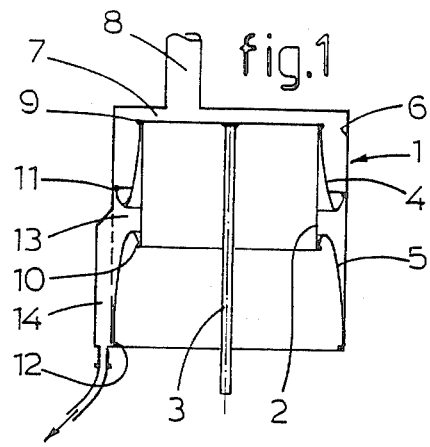
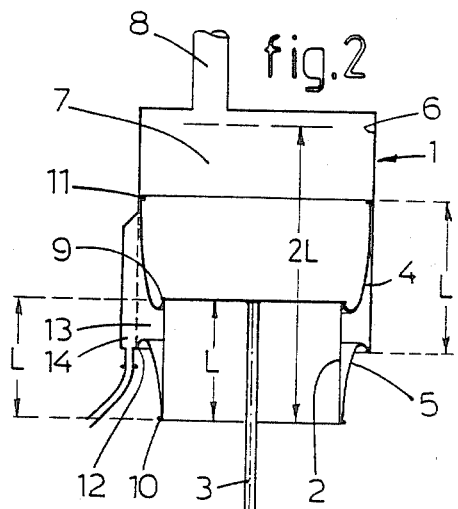
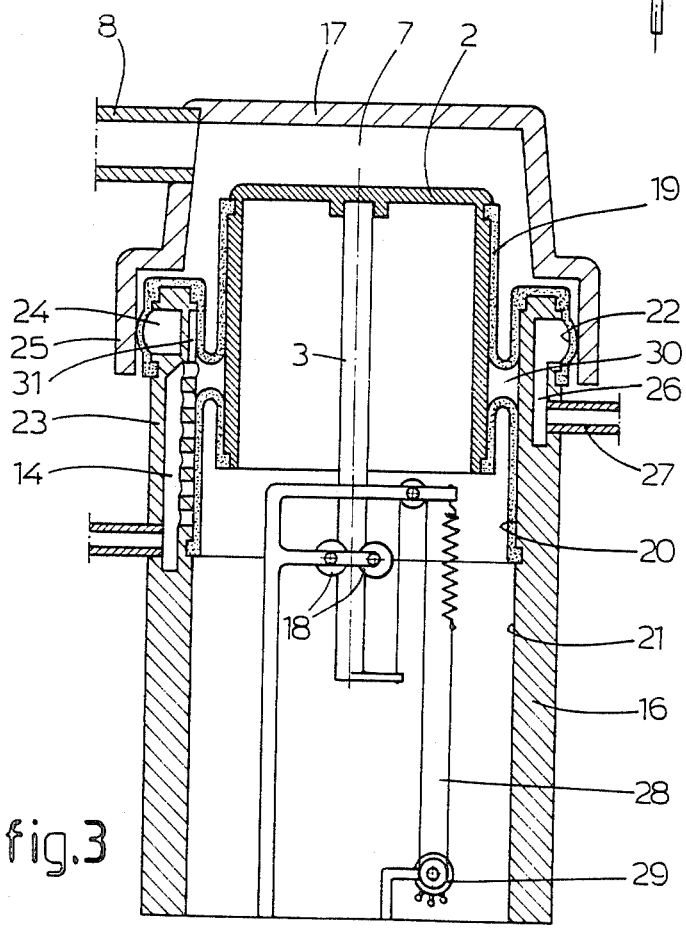

DEVICE FOR MEASURING THE VOLUME OF A GAS

BACKGROUND OF THE INVENTION

The invention relates to a device for measuring the volume of a gas, comprisng a cylinder and a piston movably mounted in said cylinder, a first membrane for sealingly connecting said piston with the inner wall of said cylinder, said cylinder, said piston and said first membrane determining a measuring space in which a measuring conduit for the gas to be measured debouches.

Such a device is known from Dutch patent application No. 67.07816. In order to make a measurement as accurate as possible with a device of this type, the piston should be movable in the cylinder as easy as possible, i.e. at a pressure increase as low as possible. To this end the membrane should unroll smoothly at the movement of the piston. In order to fulfil this requirement a thin film of flexible material is chosen as membrane at the known device, wherein for a correct unrolling the space between the piston and the cylinder inner wall must be chosen small. This results in the disadvantage of a strong bend in the membrane and thereby in frictional losses.

During use of the device when sucking or blowing in the measuring space, the pressure in the measuring space may become negative or positive with respect to the ambient pressure. Depending of the position of the membrane with respect to the measuring space, the membrane will come off from the piston or the cylinder inner wall and drag with itself. This results not only in further frictional losses but moreover an unallowable measuring error will occur as a movement of the membrane transveers to the longitudinal axis of the cylinder causes a volume variation of the measuring space without a movement of the piston so that this volume variation is not determined.

It is noted that a cylinder piston assembly is known, in which the piston is sealingly connected with the cylinder through a membrane and in which a transverse movement of the membrane is obviated by generating a pressure difference across the membrane. However in this case a restriction is provided in the discharge conduit connected to the space determined by the piston, the cylinder and the membrane. The use of such a restriction is not allowable at the device according to the invention as an accurate gas volume measurement can not be made anymore.

SUMMARY OF THE INVENTION

The invention aims to provide a device of the above-mentioned kind in which said disadvantages are eliminated.

To this end the device according to the invention is characterized in that the piston is connected with the cylinder inner wall by a second membrane, said first and second membranes determining an intermediate space, wherein an underpressure prevails in said intermediate space during operation.

Due to the pressure difference between the measuring space and the intermediate space between both membranes, the membranes will tightly be in contact with the piston wall and the cylinder inner wall. Therefore, the membranes are made stiff for pressure differences without an adverse effect on the smoothness for unrolling of the membranes. In this manner movements of the membranes transverse to the longitudinal axis are prevented so that no undesired volume variations in the measuring space can occur.

Moreover the space between the piston and the cylinder inner wall can be chosen bigger, whereby the frictional losses caused by the unrolling of the membranes are substantially decreased. Further the underpressure in the intermediate space between the membranes has a stabilizing effect on the piston. The central position of the piston in the cylinder forms a stable balance whereby the bearing of the piston can be made simpler and in principle only has to prevent a turn over of the piston. Thereby the friction of the bearing of the piston can be lowered and the device can be manufactured at lower costs.

According to a suitable embodiment of the invention the axial distance between the connection places of the membranes with the piston and the cylinder inner wall, respectively, corresponds substantially with the half of the maximum stroke of the piston.

When using a perfectly airtight material for the membranes, the intermediate space between the membranes can be brought at partial vacuum once-only.

As an alternative according to an embodiment of the invention an axially extending channel is formed in the cylinder wall between the connection places of the membranes with the cylinder inner wall, said channel being accessible from the cylinder along its entire axial length, wherein a source of underpressure can be connected to the intermediate space through the channel.

Preferably, the axial length of said piston and of both said membranes substantially equals the half of the maximum stroke of the piston, wherein the membranes are connected with the piston at the respective axial ends thereof. Thereby the piston can have a lighter construction whereby the mass inertia forces can be decreased.

BRIEF DESCRIPTION OF THE DRAWINGS

The invention will hereinafter be further explained by reference to the drawings in which some embodiments are shown.

FIGS. 1 and 2 each show a schematic diagram of an embodiment of the device according to the invention, the piston being shown in two possible end positions.

FIG. 3 is a schematically shown section of a practical embodiment of the device according to FIGS. 1 and 2.

DETAILED DESCRIPTION OF THE PREFERRED EMBODIMENTS

Referring to FIGS. 1 and 2 there is schematically shown a device for measuring a volume of a gas comprising a cylinder 1 and a piston 2 movably mounted in the cylinder 1 and having a piston rod 3. The piston 2 is sealingly connected with the cylinder inner wall 6 by means of a first membrane 4 and a second membrane 5. The cylinder 1, the piston 2 and the first membrane 4 together determine a measuring space 7, in which a measuring conduit 8 for the gas to be measured debouches. As shown in FIG. 2 The axial distance, L, between the connection places 9 and 10 of the membranes 4, 5 with the piston 2 having an axial length L and the axial distance, L, between the corresponding connection places 11 and 12 with the cylinder inner wall 6 substantially corresponds with the half of the maximum stroke 2L of the piston 2. FIG. 1 shows the piston 2 in an end position in which the measuring space 7 is minimal whereas FIG. 2 shows the piston 2 in the end positon in which the measuring space 7 is maximal.

Measuring a volume of a gas is done with the described device by supplying the gas to the measuring space 7 through the measuring conduit 8. The piston 2 will thereby be moved from a certain starting position, which movement can be measured easily and forms a measure for the supplied amount of gas. Further in this manner it is also possible to measure an amount of gas discharged from the measuring space 7.

The device is suited for example as spirometer for measuring the respiration capacity of a patient.

The axial length of the piston 2 and of the membranes 4, 5 substantially equals the half of the maximum stroke of the piston 2. The construction of the piston 2 can thereby be relatively light. The membranes 4 and 5 are connected with the piston 2 at the respective axial ends thereof. The term "substantially equal to" half the maximum stroke of the piston with respect to the distances between connection places 9, 10 and 11, 12 and the axial length of the piston 2 and the membranes 4, 5 means that such distances and lengths are equal to each other within conventional tolerance limits occurring in the construction of the device but in no event of such a length that the membranes 4, 5 would contact each other.

Thereby, the membranes 4 and 5 determine a minimal intermediate space 13 which is accessible through an axial channel 14 formed on the cylinder 1. The channel 14 is connectable to a source of underpressure in a manner not further shown and is accessible from the cylinder 1 along its whole axial length.

Thereby, during operation an underpressure can be generated in the intermediate space 13, which underpressure is chosen in such a manner that it will always be lower than the underpressure which may occur in the measuring space 7. The membrane 4 will be forced in such a position that the measuring space 7 is maximal. A movement of the membrane 4 transverse to the longitudinal axis of the device is not possible so that undesired volume variations can not occur. The membranes 4 and 5 will as tightly as possible lie against the piston wall and the cylinder inner wall 6, respectively. The membranes 4, 5 are made as if they are stiff for pressure differences. A smoothly unrolling at axial movements of the piston 2 remains possible.

It is not longer required to make the space between the piston 2 and the cylinder inner wall 6 as small as possible so that this space can be chosen relatively big. Thereby the membranes 4, 5 can unroll more smoothly so that the frictional losses will be very low.

At the embodiment of FIGS. 1 and 2 the membranes 4, 5 need not to be enclosed between the piston 2 and the cylinder inner wall 6 along the whole stroke of the piston 2. For this reason the piston 2 can have said short axial length.

The described device further has the advantage that the underpressure in the intermediate space 13 has a stabilizing effect. The central position of the piston 2 in the cylinder 1 forms a stable balance whereby a very simple bearing of the piston 2 in the cylinder 1 will suffice. This bearing principly only has to prevent a turn over of the piston. The frictional losses of the bearing can thereby be restricted, whereas the overall construction length of the device can be small.

FIG. 3 schematically shows a cross-section of the device for measuring the volume of a gas mainly corresponding with the device according to FIGS. 1 and 2.

The device according to FIG. 3 is provided with a cylinder 16 comprising at the side of the measuring space 7 a cap 17 detachably and sealingly mounted on the cylinder 16. The piston 2 with the piston rod 3 is movably borne in the cylinder 16 by means of two rollers 18 and the piston 2 is sealingly connected with the cylinder inner wall 21 by membranes 19 and 20. The membrane 19 adjacent the measuring space 7 has an end edge 22 engaging the outer wall 23 of the cylinder 16 and sealing an annular channel 24 in the outer wall 23. The cap 17 with an edge 25 surrounds the end edge 22 of the membrane 19. The annular channel 24 is connected to a source of overpressure not shown through a channel 26 and a connecting conduit 27, so that due to the overpressure in the channel 24 the end edge 22 of the membrane 19 is sealingly pressed against the inner side of the edge 25 of the cap 17. By removing the overpressure the cap 17 can be easily removed and cleaning and sterilizing of the device can be done simply and thoroughly.

It is noted that the feature of a simple and thorough sterlization possibility of the described device is of importance as the device can be used for measuring the respiration capacity of a patient. At an unsufficient sterilization of the device it could easily happen that disease-germ are conveyed through the device which of course is a severe drawback the more so as the patients involved have generally less resistance.

At the device of FIG. 3 the channel 14 for the connection of the source of underpressure is formed in the wall of the cylinder 16. In the position of the piston 2 shown in FIG. 3 a plurality of grooves 30 join the space 31 between the membranes 19 and 20, which grooves 30 are regularly distributed along the circumference of the cylinder 16 and extend in the direction of the measuring space 7. Only one of the grooves 30 is shown in FIG. 3. Due to the grooves 30 the membrane 19 will always be tightly in contact with the inner wall 21.

At the device according to FIG. 3 a possible manner for measuring the movement of the piston 2 is shown. The piston rod 3 is coupled through a cord 28 with a potentiometer 29 so that a signal will be provided by the potentiometer 29 which signal corrsponds with the movement of the piston 2.

It is noted that when a complete airtight material is used for the membranes it is possible to provide a partial vacuum in the intermediate space between the membranes once and to seal the intermediate space air-tight.

Although the described device is shown in the drawings with its axis in vertical direction, the device can be used in any position.

The invention is not restricted to the above-described embodiments which can be varied in a number of ways within the scope of the invention.

I claim:

1. Device for measuring the volume of a gas, comprising a cylinder and a piston movably mounted in said cylinder, a first membrane for sealingly connecting said piston with the inner wall of said cylinder, said cylinder, said piston and said first membrane determining a measuring space, a measuring conduit for the gas to be measured, which measuring conduit debouches in said measuring space, a second membrane for sealingly connecting said piston with the cylinder inner wall, said first and second membranes determining an intermediate space, wherein a pressure lower than the pressure in said measuring space prevails in said intermediate space during operation, and wherein the axial distance between the connection places of the membranes with the piston and the cylinder inner wall, respectively, is substantially equal to half of the maximum stroke of said piston such that said membranes remain free from each other at all positions of said piston within said cylinder.

2. Device according to claim 1, further comprising an axially extending channel in the cylinder wall between the connection places of said membranes with the cylinder inner wall and groove means connecting said channel and said intermediate space along the entire axial channel length, wherein a source of pressure lower than the pressure in said measuring space is connected to said intermediate space through said channel.

3. Device according to claim 1, wherein the axial length of said piston and of both of said membranes substantially equals half of the maximum stroke of said piston, wherein said membranes are connected with said piston at the respective axial ends thereof.

4. Device according to claim 2, wherein the axial length of said piston and of both of said membranes substantially equals half of the maximum stroke of said piston, wherein said membranes are connected with said piston at the respective axial ends thereof.

5. Device according to claim 1, wherein said cylinder at the side of said measuring space is provided with a cap detachably and sealingly mounted on said cylinder, said first membrane adjacent the measuring space has an end edge engaging the outer wall of said cylinder, the cylinder wall includes an annular channel behind said end edge, said cap surrounds said end edge of said first membrane, and said annular channel is connectable to a pressure source delivering a pressure higher than the pressure between said cap and said end edge for sealing and clampingly pressing said end edge of said first membrane against said cap.

6. Device for measuring the volume of a gas, comprising a cylinder and a piston movably mounted in said cylinder, a first membrane for sealingly connecting said piston with the inner wall of said cylinder, said cylinder, said piston and said first membrane determining a measuring space, a measuring conduit for the gas to be measured, which measuring conduit debouches in said measuring space, a second membrane for sealingly connecting said piston with the cylinder inner wall, said first and second membranes determining an intermediate space, wherein a pressure lower than the pressure in said measuring space prevails in said intermediate space during operation, the axial distance between the connection places of the membranes with the piston and the cylinder inner wall, respectively, being substantially equal to half of the maximum stroke of the piston, wherein an axially extending channel is formed in the cylinder wall between the connection places of the membranes with the cylinder inner wall and includes groove means connecting said channel and said intermediate space along the entire axial channel length wherein a source of pressure lower than the pressure in said measuring space is connected to said intermediate space through said channel and the axial length of said piston and of both of said membranes is substantially equal to half of the maximum stroke of said piston, said membranes being connected with the piston at the respective axial ends thereof.

7. Device for measuring the volume of a gas, comprising a cylinder and a piston movably mounted in said cylinder, a first membrane for sealingly connecting said piston with the inner wall of said cylinder, said cylinder, said piston and said first membrane determining a measuring space in which a measuring conduit for the gas to be measured debouches, wherein a second membrane is provided for sealingly connecting said piston with the cylinder inner wall, said first and second membranes determining an intermediate space, wherein a pressure lower than the pressure in said measuring space prevails in said intermediate space during operation, said cylinder at the side of said measuring space being provided with a cap detachably and sealingly mounted on said cylinder, wherein said first membrane adjacent said measuring space has an end edge engaging the outer wall of said cylinder, said cylinder including an annular channel in the cylinder wall behind said end edge and wherein said cap surrounds said end edge of said first membrane, said annular channel being connectable to a pressure source delivering a pressure higher than the pressure between said cap and said end edge for sealingly and clampingly pressing said end edge of said first membrane against said cap.

* * * * *